United States Patent
Binner et al.

[11] Patent Number: 6,110,403
[45] Date of Patent: Aug. 29, 2000

[54] METHOD OF PRODUCING A SYNTHETIC YARN

[75] Inventors: Tobias Binner, Remscheid; Hermann Westrich, Wuppertal, both of Germany

[73] Assignee: Barmag AG, Remscheid, Germany

[21] Appl. No.: 09/283,078

[22] Filed: Mar. 31, 1999

[30] Foreign Application Priority Data

Apr. 1, 1998 [DE] Germany .......................... 198 14 496

[51] Int. Cl.[7] .............................. D01D 5/08; D01D 7/00; D02G 3/00; G08B 21/00
[52] U.S. Cl. ................... 264/40.1; 264/103; 264/211.12; 264/211.14; 340/677; 700/144
[58] Field of Search .................................. 264/40.1, 103, 264/211.12, 211.14; 340/677; 700/144

[56] References Cited

U.S. PATENT DOCUMENTS 5,469,149  11/1995  Binner et al. .
5,844,494  12/1998  Spahlinger et al. .

FOREIGN PATENT DOCUMENTS 0 580 071   1/1994   European Pat. Off. .
WO 94/25869 11/1994  WIPO .

*Primary Examiner*—Leo B. Tentoni
*Attorney, Agent, or Firm*—Alston & Bird LLP

[57] ABSTRACT

A method of producing a synthetic yarn, wherein a yarn is spun and wound in a continuous process. For monitoring the quality, several process parameters are continuously measured. From measured data variations of the process parameters that occur within a predetermined period of time, a quality value is determined that is a measure for the regularity of the production process.

17 Claims, 3 Drawing Sheets

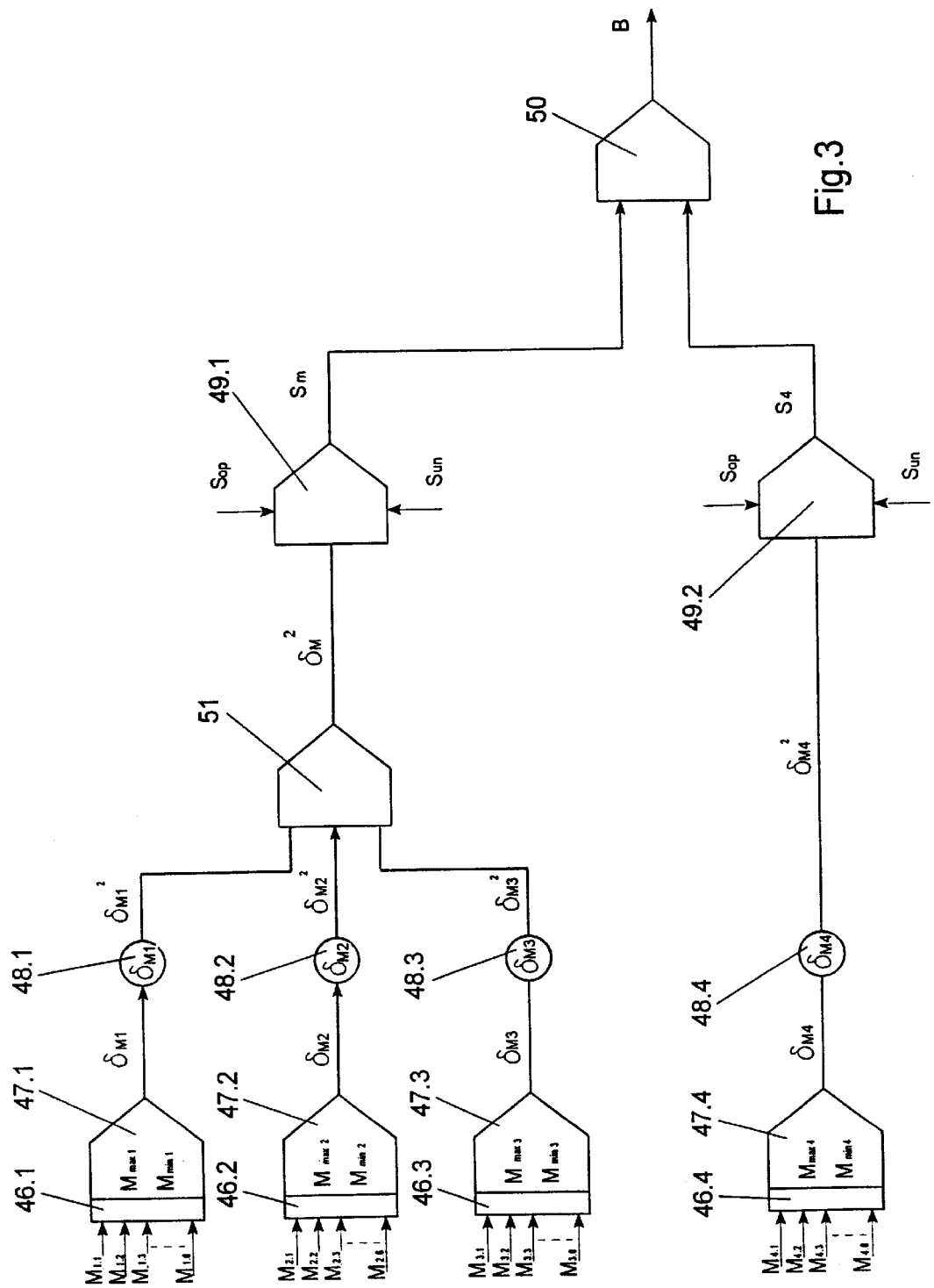

METHOD OF PRODUCING A SYNTHETIC YARN

BACKGROUND OF THE INVENTION

The invention relates to a method of producing a synthetic yarn which is wound into a yarn package.

A method of the described type is disclosed in WO 94/25869, and corresponding U.S. Pat. No. 5,844,494 which is characterized in that for monitoring the process several process parameters are measured and evaluated each in a comparison between actual and desired values. When the measured values simultaneously deviate from the desired values, a quality signal will be generated that characterizes the deviation from a normal course of the process.

In the known method, the desired values of the measured process parameter must be known. In this connection, the desired value of a machine parameter represents the adjustment of the machine parameter in an optimal course of the process that results in the production of a yarn with predetermined properties.

It is therefore an object of the invention to provide a method of producing a yarn of the initially described kind, wherein a value representative of the quality of the produced yarn is continuously derived. This value permits a classification of the end product and/or a process control.

SUMMARY OF THE INVENTION

The above and other objects and advantages of the present invention are achieved by the provision of a melt spinning and winding process which includes continuously monitoring a plurality of process parameters, and including determining a quality value from measured data variations of the process parameters that occur within a predetermined time period.

The above invention is distinguishable from the method disclosed in EP O 580 071 and corresponding U.S. Pat. No. 5,469,149. In the prior method, a continuously measured parameter of state of the package or a value derived therefrom is compared with a desired value. In the case of an unacceptable deviation of the parameter of package state or derived value from the desired value, a quality signal is generated. Likewise, in this instance, the knowledge of a desired value that is decisive for the production of the yarn is a prerequisite for monitoring the process. However, in a complex spinning process it is quite possible that based on the plurality of process parameters, a single adjustment will not exclusively lead to an optimal result. The interaction of the process parameters is very complex in particular in a spinning process. It is possible to demonstrate by the example of a yarn cohesion that is produced by an initial lubrication and a subsequent entanglement, that deviations of two process parameters may cancel each other in their effect. If the lubricant application is too low, an inadequate yarn cohesion will be produced. However, this inadequate yarn cohesion can be compensated by an increased air pressure in an entanglement nozzle upstream of a takeup device. The increased air pressure leads to an increased number of interlacing points within the yarn. Although the lubrication device and the entanglement nozzle do not operate in the desired value range, a yarn with a satisfactory cohesion is wound to a package.

The invention is therefore based on the recognition that in the production of a yarn, the quality of the yarn is substantially dependent on the regularity of the course of the process. The special advantage of the invention lies in that the quality value renders a combining statement about the state of the process and the quality of the product. In this connection, the quality value is determined alone from measured data variations of the process parameters within a period of time. The measured data variations give not only direct account of the course of the process and the actual process situation, but on the other hand also of the state of the product.

When determining the measured data variations of the process parameters, there are at least two possibilities. In a first possibility, a mean value, a maximum value, and a minimum value are initially determined from the measured values that are continuously acquired for a process parameter within a period of time. By forming the difference between the mean value and the minimum value or by forming the difference between the maximum value and the mean value, the greatest variation of the measured values is computed. This variant of the method is especially advantageous to apply to the process parameters that permit a deviation from the optimum of the process parameter in both directions. An example would be the surface temperature of a heated godet. The surface temperature can result both in a too high and in a too low surface temperature, when the heater is controlled within the godet.

In a second possibility of determining the measured data variation, a maximum value and a minimum value are computed from the measured values of the process parameters that are obtained within a period of time. The measured data variation will then result from the difference between the maximum value and the minimum value of the measured data. This variant of the method is especially advantageous in the case of the process parameters for which every effort is made to obtain a limit state as an optimum. For example, in the production of polyamide yarns, it is necessary that the winding tension be as low as possible. Thus, a measuring device of the yarn tension that is placed in the yarn path directly upstream of the takeup device would have to indicate a lowest possible value. It would then be possible to compute thus advantageously the measured data variation of this process parameter by forming the difference from a maximum value and a minimum value.

Since the quality monitoring occurs by several, often very different process parameters, a variant of the method which is particularly suitable involves the compiling of the steps of the two above possibilities. To be able to compare the measured data variations of the process parameters with one another, it is further proposed to convert the measured data variation into a relative value by division with the measured value. In this instance, it is possible to use as divisor the minimum value, the mean value, or the maximum value of the respectively measured value. The selection of the divisor makes it possible to determine a quality-rated measured data variation. Thus, a measured data variation based on the minimum value will always result in a greater relative value in comparison with the same measured data variation based on the mean value. Consequently, this variant of the method is also especially suited for evaluating the measured values of the process parameters, wherein the deviations from a mean value result in different quality deviations.

A particularly advantageous further development of the invention makes it possible to relate all determined measured data variations of the process parameters to a uniform value range and, thus, to perform a direct comparison or rating. In this connection, the measured data variations are scaled between two limit values. One of the limit values represents the optimal course of the process with an absolute regularity. This limit value is designated as Sop. The limit value Sop thus characterizes a course of the process, in which measured data variations are absent or only minimal measured data variations occur.

The second limit value of the scaling Sun, however, characterizes a course of the process, in which unacceptable measured data variations occur. The acceptable measured data variation is dependent on the process parameter. Thus, for example, a measured data variation of 10% in the case of the yarn speed may be rated unacceptable. In comparison therewith, a measured data variation of 10% at the air pressure of an entanglement nozzle may still be considered a quite acceptable measured data variation. Likewise, the scaling of the measured data variations is dependent on the product. Thus, it is quite possible that the acceptable measured data variations are predetermined in a product-specific manner. For example, the measured data variations of the speed of godets in the production of a POY yarn may differ in comparison with the production of an FDY yarn.

Thus, it is possible to determine the quality value directly from the entirety of the scale values that are defined by the measured data variations. In this connection, it will be particularly advantageous to compute the quality value by an arithmetic mean value of the individual scale values. However, it is also possible to weight the individual scale values and to form a mean value thereafter.

In a particularly advantageous variant of the method, the measured data variations of equivalent process parameters are combined and scaled only once. In this instance, similar process parameters are the parameters that have the same physical quantity as measured value. These could include, for example, all yarn tensions measured in a process or all godet speeds measured in the process.

In the method of the present invention, the quality value B is related to a period of time. This means that the process has produced a yarn of the determined quality within the predetermined period of time. It will thus be especially advantageous, when the period of time equals the time for winding a complete package. With that, it will be possible to associate a quality value to each fully wound package, which is of special advantage in particular for the further processing of the wound yarn. This also facilitates a classification of the produced packages without problems. To this end, the determined quality value is associated to the finished package. A subsequent quality sorting will occur with consideration of the quality value of the package.

Especially advantageous is the variant of the method wherein a control unit with an output unit is provided for displaying the quality value in visual form after winding the complete package. With that, the relationship between the package and the determined quality value remains intact even after removal. The readout may occur electronically in the form of data transmissions, or even in visual form directly on the package, for example, by imprints or other optical identifications.

The method of the present invention is also especially suitable for intervening directly in a production process. To this end, it is possible to equalize, for example, the determined quality value with a previously determined maximum value. Should the quality value exceed the maximum value, it will be necessary to intervene in the production process. When these limits are exceeded, it will be possible to selectively release a diagnosis signal, recommend a package doff, perform a package doff, or shut down the entire line.

It is possible to control the production process especially advantageously as a function of the measured data variations. Thus, it becomes possible to influence the respective process parameters in a purposeful manner. Furthermore, there exists the possibility of separately controlling especially critical process parameters.

Since in the production of a synthetic yarn only the interaction of many parameters leads to a qualitatively superior yarn, it may be advantageous to establish user-defined control systems that effect a process intervention by one or more logical interconnections. In the simplest manner, the logical interconnection may consist in that a process change will occur, if the measured data variation δM1 of the process parameter M1 is greater than the measured data variation δM2 of the process parameter M2, and the measured data variation δM3 of the process parameter M3 is smaller than the measured data variation δM4 of the process parameter M4. By such logical interconnections, it is possible to draw with advantage conclusions as to possible causes in the case of unacceptable deviations of the measured values.

To determine the quality value, it is possible to monitor machine parameters, yarn parameters, and/or package parameters. As machine parameters, one may select in particular output-related quantities, such as power, active power, phase angle, or slip of the drives of, for example, godets, spin pumps, lubricant pumps, and extruders. Likewise, it is possible to monitor as machine parameters the temperatures of all heaters. Basically, it is possible to monitor as machine parameters any physical quantity that is measurable in the course of the process, such as, for example, melt pressure on the extruder, air pressure of the entanglement nozzle.

Besides the melt composition, it is possible to monitor as yarn parameters the yarn tensions, yarn speeds, lubricant application, number of knots, or yarn temperature. The yarn tension can be measured with yarn tension sensors, or by power measurement of two godets that follow each other in the path of the yarn.

Package parameters that may be used for monitoring include in particular the diameter increase per unit time as well as the package weight.

BRIEF DESCRIPTION OF THE DRAWINGS

In the following the method as well as a spinning line for carrying out the method are described with reference to drawings, in which:

FIG. 3 is a schematic view of a further signal flow for determining the quality value B.

DETAILED DESCRIPTION OF THE PREFERRED EMBODIMENTS

Figure 1:
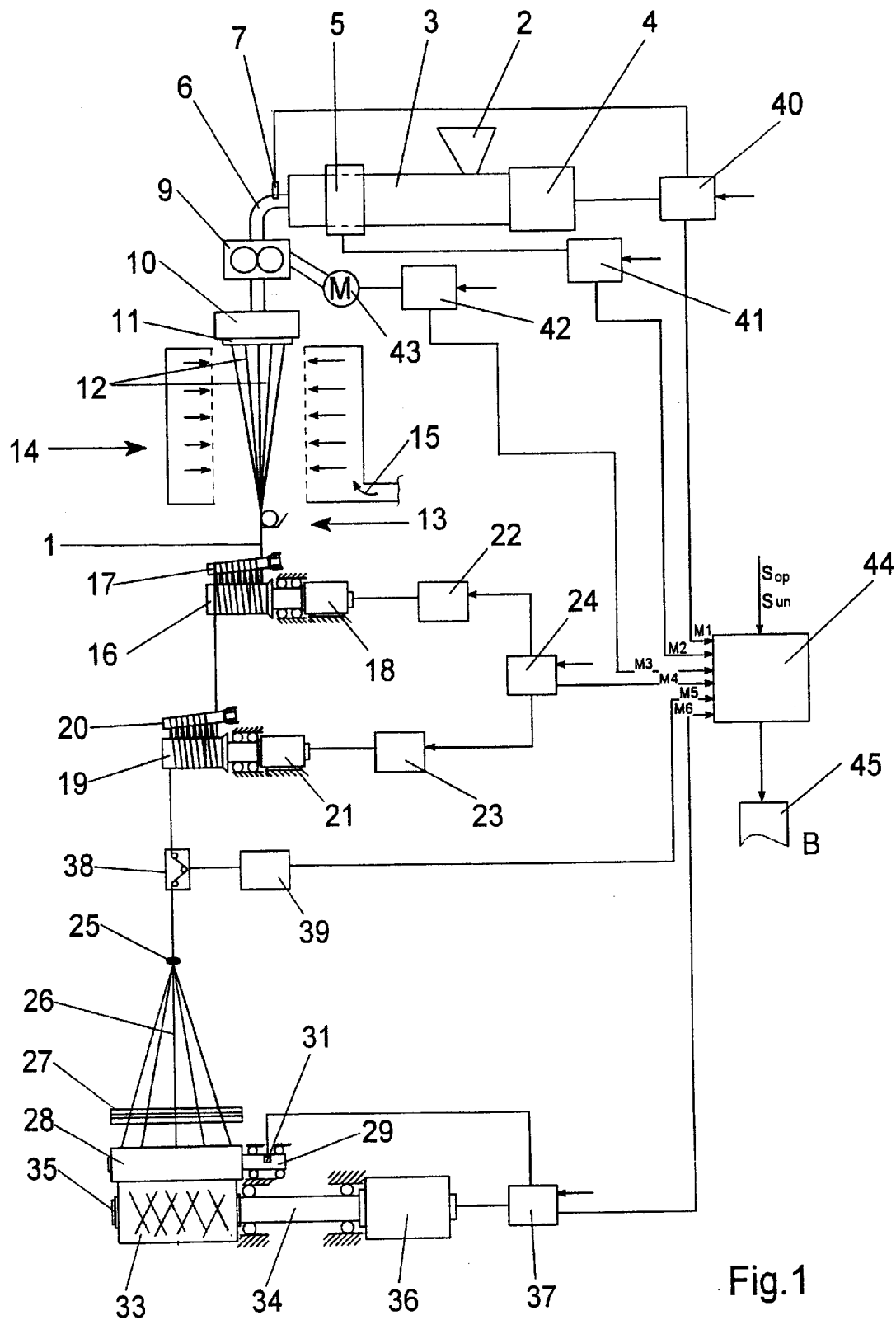
FIG. 1 is a schematic view of a spinning line with the process stages spinning, drawing, and winding.

FIG. 1 illustrates a spinning line for producing a yarn 1 from a thermoplastic material. The thermoplastic material is supplied through a hopper 2 to an extruder 3. A motor 4 drives the extruder 3. An extruder controller 40 controls the motor 4. In the extruder 3 the thermoplastic material is melted. Within the extruder 3, a heater 5 tempers the material. The heater 5 connects to a heating controller 41. The heater 5 is, for example, a resistance heater.

A melt line 6 connects to the outlet end of extruder 3. The melt line 6 accommodates a pressure sensor 7 for measuring the melt pressure for a pressure-speed control of the extruder. The pressure sensor 7 connects to the extruder controller 40. Through the melt line 6, the melt advances to a spin pump 9. The spin pump 9 is operated by a pump drive 43. A pump controller 42 activates the pump drive 43 such that the pump speed is finely adjustable. The spin pump 9 delivers the melt flow to a heated spin head 10. The underside of spin head 10 mounts a spinneret 11. From the spinneret 11, the melt emerges in the form of strands of fine filaments 12. The filament strands 12 advance through a cooling device 14. In the cooling device 14, an air stream 15 is directed by blowing transversely or radially to the web of filaments 12, thereby cooling the filaments 12.

At the outlet end of cooling device 14, a lubricant applicator 13 combines the web of filaments 12 to a yarn 1 and applies to same a liquid lubricant. From the cooling device 14 and spinneret 11, the yarn is withdrawn by a godet 16. The yarn loops about a withdrawal godet 16 several times. To this end, use is made of a guide roll 17 that is arranged with its axis inclined relative to the godet 16. The guide roll 17 is freely rotatable. The godet 16 is driven by a godet drive 18 that is activated by a frequency changer 22 at a preadjustable speed. The withdrawal speed is by a multiple higher than the natural exit speed of the filaments 12 from spinneret 11.

Downstream of withdrawal godet 16, a draw godet 19 is arranged with a further guide roll 20. Both correspond in their construction to withdrawal godet 16 with guide roll 17. A godet drive 21 with a frequency changer 23 serves to drive draw godet 19. The frequency changers 22 and 23 are activated via a godet controller 24. In this manner, it is possible to adjust on frequency changers 22 and 23 individually the rotational speed of withdrawal godet 16 and draw godet 19 respectively.

From the draw godet 19, the yarn 1 advances to a yarn guide 25 and thence to a traversing triangle 26. At the end of the traversing triangle, a traversing device 27 is arranged. The traversing device may be a rotary blade-type or a cross-spiraled roll-type traversing system. In both cases, the yarn is reciprocated by means of one or more yarn guides within a traverse stroke substantially transversely to its direction of advance. In so doing, the yarn advances onto a contact roll 28 downstream of the traversing device. From the partially looped contact roll 28, the yarn then reaches a package 33 and is wound thereon. The contact roll 28 lies against the surface of package 33. It is used to measure the surface speed of package 33. The package 33 is wound a tube 35. A winding spindle 34 mounts the tube 35. The winding spindle 34 is driven by a spindle motor 36 that is controllable by a spindle control unit 37. The spindle control unit 37 activates the spindle motor 36 in such a manner that the surface speed of package 33 remains substantially constant. To this end, the speed of rotatable contact roll 28 is measured on a shaft 29 by means of a sensor 31 and supplied as a controlled variable to spindle control unit 37.

Between draw godet 28 and the takeup device, a yarn tension sensor 38 is arranged in the path of the advancing yarn. The yarn tension sensor 38 connects to a measuring device 39. The measuring device 39 connects again via a signal line to a control unit 44. The control unit 44 connects likewise, respectively via one signal line, to extruder controller 40, to heating controller 41, to pump controller 42, to godet controller 24, and to spindle control unit 37. Via the signal lines, the measured values of the process parameters $M_1$ to $M_6$ are supplied to the control unit 44. In this connection, $M_1$ may be pressure of the melt, $M_2$ the temperature, $M_3$ the rotational speed of the pump, $M_4$ the speed ratio between the draw godet and the withdrawal godet, $M_5$ the yarn tension, and $M_6$ the package diameter.

Within the control unit 44, the process parameters $M_1$ to $M_6$ are evaluated as measured data, scaled, and converted into a quality value B. The control unit 44 connects to an output unit 45 that facilitates a display or readout of the quality value B.

Figure 2:
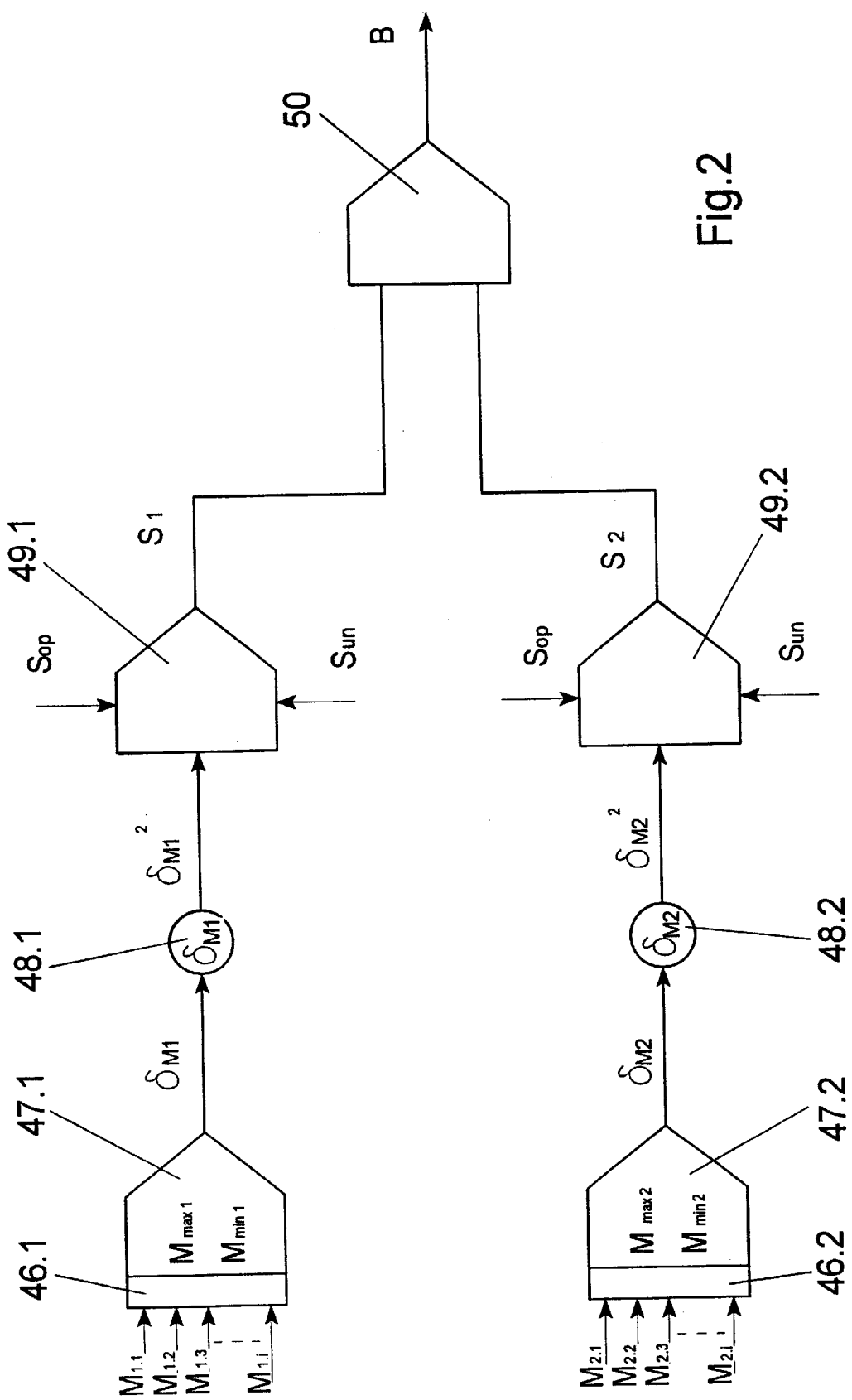
FIG. 2 is a schematic view of a signal flow for determining a quality value B.

FIG. 2 schematically illustrates by the example of two process parameters, how the measured values of the process parameters are converted within the control unit 44 to a quality value B. To begin with, the measured data of the respective process parameter are supplied to a time filter 46. The time filter 46 has a time constant that corresponds to a predetermined period of time. Thus, only data of the process parameter that were measured within a time unit are supplied by the time filter to an adjacent computing unit 47. In FIG. 2, the measured data of the two process parameters are indicated at $M_1$ and $M_2$. From the plurality of the measured data of the first process parameter $M_{1.1}$ to $M_{1.i}$, the computing unit 47.1 computes a mean value $M_{M1}$ as well as a maximum value $M_{max1}$ and a minimum value $M_{min1}$. From the mean value, the maximum value, and the minimum value the computing unit computes the greatest measured data variation $\delta_{M1}$. The computation occurs in this instance by a simple difference formation from the equation $\delta_{M1} = M_{max1} - M_{M1}$ or $\delta_{M1} = M_{M1} - M_{min1}$. Subsequently, the thus-determined value of the measured data variation $\delta_{M1}$ is squared by a squarer 48.1. The squared individual result of the measured data variation $\delta_{M12}$ is supplied to a comparator 49.1. Within the comparator 49.1, the measured data variation is scaled with reference to a stored table of values. The table of values is defined by limit values $S_{un}$ and $S_{op}$ that are supplied to the comparator. The limit value $S_{op}$ denotes a minimal measured data variation or a measured data variation with a zero value. This scale value thus corresponds to a process of greatest regularity. In comparison therewith, the second limit value Sun is predetermined as a function of the parameter and denotes the just acceptable or the unacceptable measured data variation. The value of the measured data variation $\delta_{M1}^2$ is associated with a scale value $S_1$ that is subsequently supplied to a second computing unit 50. In the computing unit 50, all scaled measured data variations are combined. In the embodiment shown in FIG. 2, only two process parameters are provided for monitoring the process. The measured data of the second process parameter $M_{2.1}$ to $M_{2.i}$ pass likewise through a time filter 46.2. In the computing unit 47.2, a maximum value $M_{max2}$ and minimum value $M_{min2}$ are computed. In the case of the second process parameter, the measured data variation is computed from the difference $\delta_{M2} = M_{max2} - M_{min2}$. After the squaring, comparator 49.2 associates to the thus determined value of the measured data variation a scale value $S_2$. The scaled value $S_2$ is combined in computing unit 50 with the scaled value $S_1$ of the first process parameter and designated a quality value B. Advantageously, the quality value B can be computed by the arithmetic mean value from the equation $B = (S_1 + S_2)/2$. Thus, the quality value B provides directly a measure for the regularity of the production process.

FIG. 3 shows a further embodiment of processing measured data by a control unit, as shown, for example, in FIG. 1. In the present embodiment, the process parameters with their measured data $M_1$, $M_2$, and $M_3$ pass each through a time filter 46 to a subsequent computing unit 47. After squaring, the determined individual measured data variations $\delta_{M1}$, $\delta_{M2}$, and $\delta_{M3}$ are added in a summator 51. The sum of the squares of measured data variation $\delta_{m2}$ is subsequently scaled in comparator 49. The computing unit 50 carries the scaled values $S_m$ and the scale value $S_4$ of a fourth parameter, and the quality value B is determined. In the embodiment shown in FIG. 3, the process parameters $M_1$, $M_2$, and $M_3$ are each monitored by a same physical quantity. This could be, for example, the speed of all godets. The processing of measured data as shown in FIG. 3 makes it possible to reduce substantially the electronic expense of a control unit.

At this point, it should be explicitly remarked that the method of the present invention is not limited to the spinning line shown in FIG. 1. Instead, because of monitoring individual process parameters by the method of the present invention, it is possible to apply any production process for the continuous production of an endless material from a thermoplastic plastic. For the monitoring, both machine parameters and product parameters are suitable. However, a prerequisite is that the parameter be measurable by a physical quantity.

Advantageously, the present invention may also be combined with quality monitoring systems of the prior art. Thus, the method of diagnosing errors as disclosed in WO 94/25869 and U.S. Pat. No. 5,844,494 can easily be combined with the method of the present invention.

What is claimed is:

1. A method of producing a synthetic yarn comprising the steps of melt spinning a polymeric material to form an advancing yarn, winding the advancing yarn to form a yarn package, continuously monitoring a plurality of process parameters, and including determining a quality value (B) from measured data variations ($\delta_M$) of the process parameters that occur within a predetermined time period, and wherein the measured data variations ($\delta_M$) of the process parameters are each converted to a scale value (S) that rates the course of the process for its regularity irrespective of the process parameter.

2. The method as defined in claim 1 wherein the measured data variations ($\delta_M$) of the process parameters are each determined by the steps of:

computing a mean value ($M_M$) from the measured data of the period of time, computing a maximum value ($M_{max}$) and a minimum value ($M_{min}$) from the measured data of the period of time, and forming the greatest measured data variation ($\delta_M$) from the difference between the mean value ($M_M$) and the minimum value ($M_{min}$) or from the difference between the maximum value ($M_{max}$) and the mean value ($M_M$).

3. The method as defined in claim 1 wherein the measured data variations ($\delta_M$) of the process parameters are each determined by the steps of:

computing a maximum value ($M_{max}$) and a minimum value ($M_{min}$) from the measured data of the period of time, and forming the measured data variation from the difference between the maximum value ($M_{max}$) and the minimum value ($M_{min}$).

4. The method as defined in claim 1 wherein the measured data variations ($\delta_M$) of the process parameters are determined by compiling (A) the steps of computing a mean value ($M_M$) from the measured data of the period of time, computing a maximum value ($M_{max}$) and a minimum value ($M_{min}$) from the measured data of the period of time, and forming the greatest measured data variation ($\delta_M$) from the difference between the mean value ($M_M$) and the minimum value ($M_{min}$) or from the difference between the maximum value ($M_{max}$) and the mean value ($M_M$), and (B) the steps of computing a maximum value ($M_{max}$) and a minimum value ($M_{min}$) from the measured data of the period of time, and forming the measured data variation from the difference between the maximum value ($M_{max}$) and the minimum value ($M_{min}$).

5. The method as defined in claim 1 wherein the measured data variations ($\delta_M$) are converted to a relative value by dividing with the measured value, the divisor being formed by the minimum value, the mean value, or the maximum value.

6. The method as defined in claim 1 wherein the scale value (S) defines the course of the process within a table of values, with the table of values being defined by two limit values ($S_{op}$; $S_{un}$), with one of the limit values ($S_{op}$) identifying the measured data variation as zero ($\delta_M=0$) and the other of the limit values ($S_{un}$) as an unacceptable measured data variation (δ=unacceptable).

7. The method as defined in claim 1 wherein the quality value (B) is determined from the entirety of the scale values (S) that are defined by the measured data variations ($\delta_M$).

8. The method as defined in claim 1 wherein the quality value (B) is computed by an arithmetic mean value of the individual scale values (S).

9. The method as defined in claim 1 wherein the period of time equals the time for winding a complete package.

10. The method as defined in claim 9 wherein a control unit with an output unit is provided to display the quality value in visual form after winding the complete package.

11. The method as defined in claim 10 wherein the completely wound package with the associated quality value is supplied to a quality sorting.

12. The method as defined in claim 1 wherein the process is controlled as a function of the measured data variations.

13. The method as defined in claim 12 wherein the measured data variations of a plurality of process parameters are linked with one another by one or more logical interconnections such that an intervention in the process occurs only while adhering to the interconnection.

14. The method as defined in claim 1 wherein the process parameters are formed by machine parameters, yarn parameters, and/or package parameters.

15. The method as defined in claim 1 wherein the melt spinning step includes forming a plurality of advancing filaments, cooling the advancing filaments, and gathering the cooled advancing filaments to form the advancing yarn.

16. A method of producing a synthetic yarn comprising the steps of melt spinning a polymeric material to form an advancing yarn, winding the advancing yarn to form a yarn package, continuously monitoring a plurality of process parameters, and including determining a quality value (B) from measured data variations ($\delta_M$) of the process parameters that occur within a predetermined time period, and wherein from the measured data variations of identical process parameters a total value is formed that is converted to a scale value.

17. A method of producing a synthetic yarn comprising the steps of melt spinning a polymeric material to form an advancing yarn, winding the advancing yarn to form a yarn package, continuously monitoring a plurality of process parameters, and including determining a quality value (B) from measured data variations ($\delta_M$) of the process parameters that occur within a predetermined time period, wherein the process is controlled as a function of the measured data variations, and wherein the measured data variations of a plurality of process parameters are linked with one another by one or more logical interconnections such that an intervention in the process occurs only while adhering to the interconnection.

* * * * *